United States Patent
Tomiha

(10) Patent No.: US 9,687,173 B2
(45) Date of Patent: Jun. 27, 2017

(54) COIL PAD, VIBRATOR, AND MAGNETIC RESONANCE IMAGING APPARATUS

(71) Applicant: TOSHIBA MEDICAL SYSTEMS CORPORATION, Otawara-shi (JP)

(72) Inventor: Sadanori Tomiha, Tochigi (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 50 days.

(21) Appl. No.: 14/463,951

(22) Filed: Aug. 20, 2014

(65) Prior Publication Data
US 2015/0057525 A1 Feb. 26, 2015

(30) Foreign Application Priority Data
Aug. 26, 2013 (JP) ................. 2013-175019

(51) Int. Cl.
| | |
|---|---|
| *G01R 33/563* | (2006.01) |
| *A61B 5/055* | (2006.01) |
| *A61B 5/00* | (2006.01) |
| *A61B 17/34* | (2006.01) |
| *G01R 33/3415* | (2006.01) |
| *G01R 33/28* | (2006.01) |
| *A61B 90/00* | (2016.01) |

(52) U.S. Cl.
CPC ............ *A61B 5/055* (2013.01); *A61B 5/0051* (2013.01); *A61B 17/3403* (2013.01); *G01R 33/3415* (2013.01); *G01R 33/56358* (2013.01); *A61B 2017/3411* (2013.01); *A61B 2090/3958* (2016.02); *G01R 33/285* (2013.01)

(58) Field of Classification Search
CPC ....... A61B 5/00; A61B 5/0048; A61B 5/0051; G01R 33/34; G01R 33/341; G01R 33/56358
See application file for complete search history.

(56) References Cited

U.S. PATENT DOCUMENTS

| | | | | |
|---|---|---|---|---|
| 2011/0245658 A1* | 10/2011 | Numano | ......... | G01R 33/56358 600/421 |
| 2013/0069651 A1* | 3/2013 | Lumiani | ......... | G01R 33/34084 324/318 |

FOREIGN PATENT DOCUMENTS

JP 2004-283372 10/2004

OTHER PUBLICATIONS

MR elastography: initial findings in Japan, GE Healthcare Japan in Navi Suite, <www.innervision.co.jp/suite/ge/advanced_report2011/1109/>, *Healthymagination series 2011*, Advanced Report No. 4, Jul. 17, 2013—retrieval date, 8 pgs w/ Machine Translation.

* cited by examiner

*Primary Examiner* — Tse Chen
*Assistant Examiner* — Jason Ip
(74) *Attorney, Agent, or Firm* — Nixon & Vanderhye P.C.

(57) ABSTRACT

A coil pad according to one embodiment is a coil pad that is placed between a receiving coil and a subject. The receiving coil is mounted on the subject and receives a magnetic resonance signal emitted from the subject. The coil pad includes a pad opening and a vibrating portion. The pad opening is aligned with a coil opening included in the receiving coil and forms a through-hole between the coil opening and the subject. The vibrating portion vibrates with a medium that transmits vibration being filled therein.

6 Claims, 15 Drawing Sheets

COIL PAD, VIBRATOR, AND MAGNETIC RESONANCE IMAGING APPARATUS

CROSS-REFERENCE TO RELATED APPLICATIONS

This application is based upon and claims the benefit of priority from Japanese Patent Application No. 2013-175019, filed on Aug. 26, 2013, the entire contents of all of which are incorporated herein by reference.

FIELD

Embodiments described herein relate generally to a coil pad, a vibrator, and a magnetic resonance imaging (MRI) apparatus.

BACKGROUND

Conventional methods for measuring the stiffness of an internal organ, such as the liver, using an MRI apparatus include an imaging method called MR elastography. In MR elastography, a vibrator is placed between a receiving coil of an MRI apparatus and a subject, and the vibrator vibrates an internal organ of the subject, whereby an MR image in which coefficients of elasticity indicating the stiffness can be obtained. In general, a region of fibrosis in an internal organ is specified in such MR elastography, and the specified region is subjected to biopsy.

DETAILED DESCRIPTION

A coil pad according to one embodiment is a coil pad that is placed between a receiving coil and a subject. The receiving coil is mounted on the subject and receives a magnetic resonance signal emitted from the subject. The coil pad includes a pad opening and a vibrating portion. The pad opening is aligned with a coil opening included in the receiving coil and forms a through-hole between the coil opening and the subject. The vibrating portion vibrates with a medium that transmits vibration being filled therein.

First Embodiment

Figure 1:
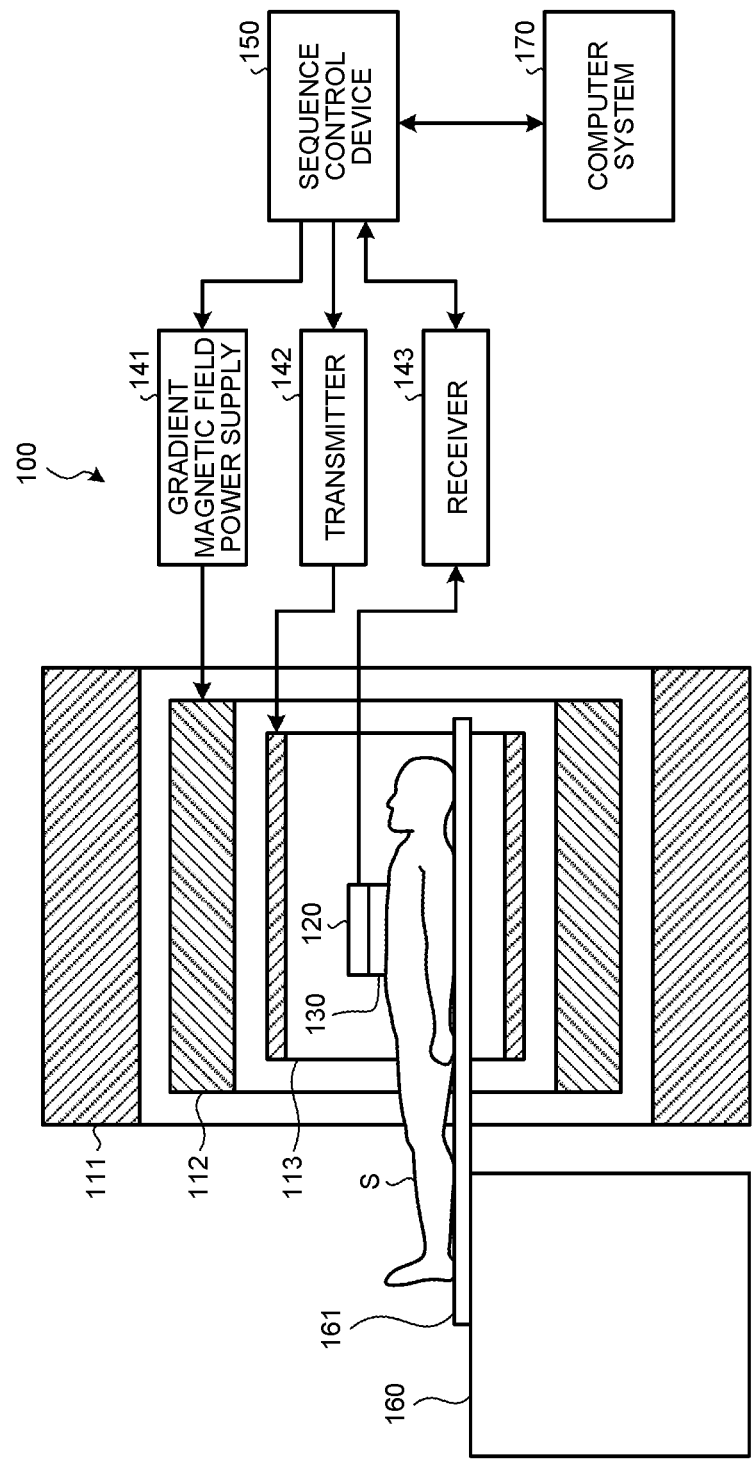
FIG. 1 is a schematic illustrating one example of the configuration of an MRI apparatus according to a first example.

FIG. 1 is a schematic illustrating one example of the configuration of an MRI apparatus according to a first example. As illustrated in FIG. 1, the MRI apparatus 100 includes a static magnetic field magnet 111, a gradient coil 112, a transmitting coil 113, a receiving coil 120, a coil pad 130, a gradient magnetic field power supply 141, a transmitter 142, a receiver 143, a sequence control device 150, a couch apparatus 160, and a computer system 170.

The static magnetic field magnet 111 is a magnet formed in a cylindrical shape. With current supplied thereto from a static magnetic field power supply, the static magnetic field magnet 111 generates a static magnetic field in a space inside a cylinder hollow (not illustrated) in which a subject S is placed.

The gradient coil 112 is a coil formed in a cylindrical shape, and is arranged inside the static magnetic field magnet 111. With current supplied from the gradient magnetic field power supply 141, the gradient coil 112 generates gradient magnetic fields in the space inside the cylinder hollow where the subject S is placed. The respective gradient magnetic fields follow three directions x, y, and z that are orthogonal to one another.

The transmitting coil 113 is a coil formed in a cylindrical shape, and is arranged inside the gradient coil 112. The transmitting coil 113 receives radio frequency current supplied from the transmitter 142 via a power supply cable, thereby generating a radio frequency magnetic field in the space inside the cylinder hollow in which the subject S is placed.

The static magnetic field magnet 111, the gradient coil 112, and the transmitting coil 113 are mounted on a gantry apparatus (not illustrated).

The receiving coil 120 is mounted on the subject S and receives magnetic resonance signals emitted from the subject S by the effect of the radio frequency magnetic field. The receiving coil 120 amplifies the received magnetic resonance signals with an amplifier included internally therein and outputs the amplified magnetic resonance signals.

The coil pad 130 is interposed between the receiving coil 120 and the subject S. With the coil pad 130 interposed between the receiving coil 120 and the subject S, a certain distance can be provided between the receiving coil 120 and the subject S corresponding to the thickness of the coil pad 130. Thus, the sensitivity of receiving coil 120 can be adjusted. Furthermore, heat generated from the receiving coil 120 can be prevented from being directly transmitted to the subject S.

The gradient magnetic field power supply 141 supplies current to the gradient coil 112 in accordance with an instruction from the sequence control device 150. For example, the gradient magnetic field power supply 141 includes a high voltage generating circuit and a gradient magnetic field amplifier. The high voltage generating circuit converts alternating current (AC) supplied from a commercial alternating-current power supply into direct current (DC) and supplies the DC to the gradient magnetic field amplifier. The gradient magnetic field amplifier amplifies the DC supplied from the high voltage generating circuit and supplies the amplified DC to the gradient coil 112.

The transmitter 142 transmits a radio frequency (RF) pulse to the transmitting coil 113 in accordance with an instruction from the sequence control device 150. For example, the transmitter 142 includes an oscillation unit, a phase selecting unit, a frequency transforming unit, an amplitude modulating unit, and an RF amplifier. The oscillation unit generates an RF pulse having a resonance frequency common to target nuclei within a static magnetic field. The phase selecting unit selects a phase for the RF pulse generated by an emission unit. The frequency transforming unit transforms the frequency of the RF pulse output from the phase selecting unit. The amplitude modulating unit modulates the amplitude of the RF pulse output from a frequency modulating unit, for example, by applying a sinc function thereto. The RF amplifier amplifies the RF pulse output from the amplitude modulating unit and supplies the amplified RF pulse to the transmitting coil 113.

The receiver 143 detects a magnetic resonance signal received by the transmitting coil 113 in accordance with an instruction from the sequence control device 150. The receiver 143 generates raw data by performing analog-to-digital (A/D) conversion on the detected magnetic resonance signal, and transmits the generated raw data to the sequence control device 150. For example, the receiver 143 includes a selector, a pre-amplifier, a phase sensitive detector, and an A/D converter. The selector selectively inputs magnetic resonance signals input from the transmitting coil 113. The pre-amplifier amplifies a magnetic resonance signal output from the selector. The phase sensitive detector detects the phase of the magnetic resonance signal output from the pre-amplifier. The A/D converter converts a signal output from the phase sensitive detector into a digital signal.

The sequence control device 150 drives the gradient magnetic field power supply 141, the transmitter 142, and the receiver 143 separately under the control of the computer system 170 so as to perform data collection. When raw data is transmitted from the receiver 143 as a result of the data collection, the sequence control device 150 transmits the raw data to the computer system 170.

The couch apparatus 160 includes a couchtop 161 on which the subject S is placed, and carries the couchtop 161 together with the subject S into an imaging space inside a bore portion provided in the gantry apparatus.

The computer system 170 controls the entirety of the MRI apparatus 100. For example, the computer system 170 includes an input unit that accepts various operations from an operator, a sequence control unit that causes the sequence control device 150 to perform data collection based on imaging conditions input by the operator, an image restructuring unit that reconstructs an image based on raw data transmitted from the sequence control device 150, a storage unit that stores therein the reconstructed image and the like, a display unit that displays various kinds of information such as the reconstructed image, and a main control unit that controls the respective functional units in accordance with instructions from the operator.

The example of the configuration of the MRI apparatus 100 according to the first embodiment is as described above. With the above-described configuration, in the MRI apparatus 100, the coil pad 130 to be placed between the receiving coil 120 and the subject S includes pad openings and a vibrating surface. The pad openings are aligned with the coil openings provided in the receiving coil 120, thereby forming through-holes between the coil openings and the subject S. The vibrating surface is provided on the side facing the subject, and vibrates with vibrating air fed into a hollow portion in the interior of the coil pad 130.

In the MRI apparatus 100 according to the first embodiment, this configuration makes it possible to use the coil pad 130 in place of a vibrator in performing MR elastography. This configuration allows a puncture needle to be inserted into the subject through the through-hole formed of the coil opening of the receiving coil 120 and the corresponding pad opening of the coil pad 130, thereby making it possible to conduct a biopsy without removing the receiving coil 120 and the coil pad 130 from the subject S after performing MR elastography.

In a conventional MRI apparatus, a vibrator is arranged so as to cover an imaging region when MR elastography is performed, and it is necessary to remove the vibrator when a biopsy is conducted. Thus, it is necessary to remove the receiving coil that covers the vibrator from the subject, detach the vibrator, and then reattach the receiving coil to the subject, after performing MR elastography. In MR elastography, typically, a biopsy target position is specified on the basis of the positional relation thereof with a biopsy grid fitted in the receiving coil. Thus reattaching the receiving coil before a biopsy may result in displacement of a biopsy target position.

In contrast, the MRI apparatus 100 according to the first embodiment allows for a biopsy without having the coil pad 130 and the receiving coil 120 removed from the subject S, and can prevent displacement of a biopsy target position after elastography. The following describes the MM apparatus 100 according to the present embodiment in detail.

Figure 2:
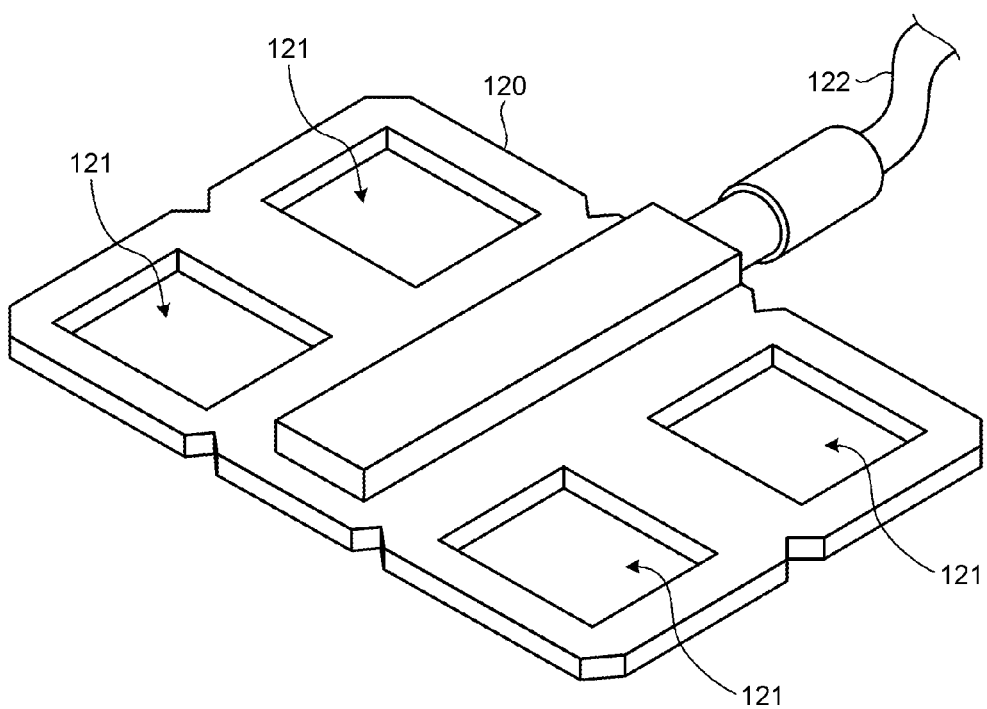
FIG. 2 is a view illustrating one example of a receiving coil according to a first embodiment.

FIG. 2 is a view illustrating one example of the receiving coil according to the first embodiment. For example, as illustrated in FIG. 2, the receiving coil 120 according to the first embodiment is a surface coil formed in a rectangular shape, and includes four coil openings 121. For example, when the MRI apparatus 100 performs MR elastography, the receiving coil 120 is attached to the subject S in such a manner as to cover an internal organ on which to conduct a biopsy. Connected to the receiving coil 120 is a power transmission cable 122 that transmits magnetic resonance signals output from the receiving coil 120 to the receiver 143.

Here, the shape of the receiving coil 120 is not necessarily limited to a rectangular shape. For example, the shape of the receiving coil 120 may be a square or circular shape. The number of coil openings 121 included in the receiving coil 120 is not limited to four, and at least one coil opening 121 may be provided.

Figure 3:
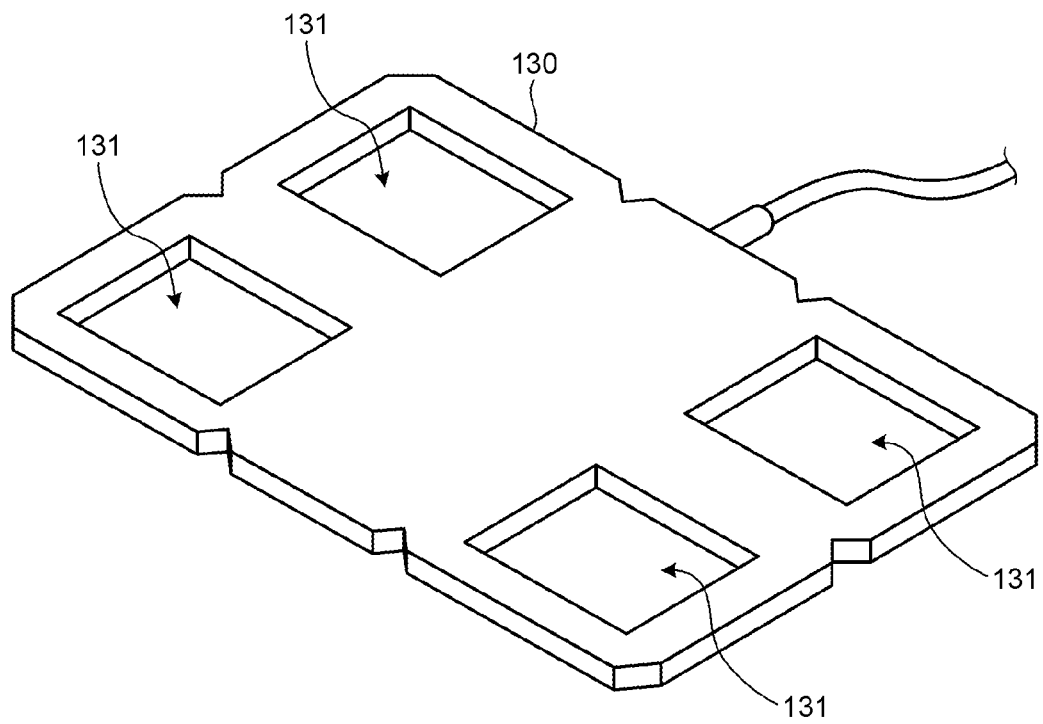
FIG. 3 is a view illustrating one example of a coil pad according to the first embodiment.

FIG. 3 is a view illustrating one example of the coil pad according to the first embodiment. For example, as illustrated in FIG. 3, a coil pad 130 according to the first embodiment is formed of a resin, such as vinyl chloride, and formed in substantially the same shape as that of the receiving coil 120. For example, when the receiving coil 120 illustrated in FIG. 2 is used, the coil pad 130 is formed in a rectangular shape as with the receiving coil 120. The coil pad 130 has pad openings 131 formed therein at positions corresponding to four coil openings 121 in the receiving coil 120.

The shape of the coil pad 130 needs not necessarily be exactly the same as that of the receiving coil 120. Specifically, the shape of the coil pad 130 may be different from that of the receiving coil 120 as long as at least one pad opening 131 is provided at a position that allows alignment thereof with the coil openings 121 when the coil pad 130 is overlapped with the receiving coil 120. Moreover, the number of pad openings 131 of the coil pad 130 need not necessarily be equal to the number of the coil openings 121 of the receiving coil 120. Specifically, at least one pad opening 131 is provided at a position that allows alignment thereof with the coil openings 121 when the coil pad 130 is overlapped with the receiving coil 120.

Figure 4:
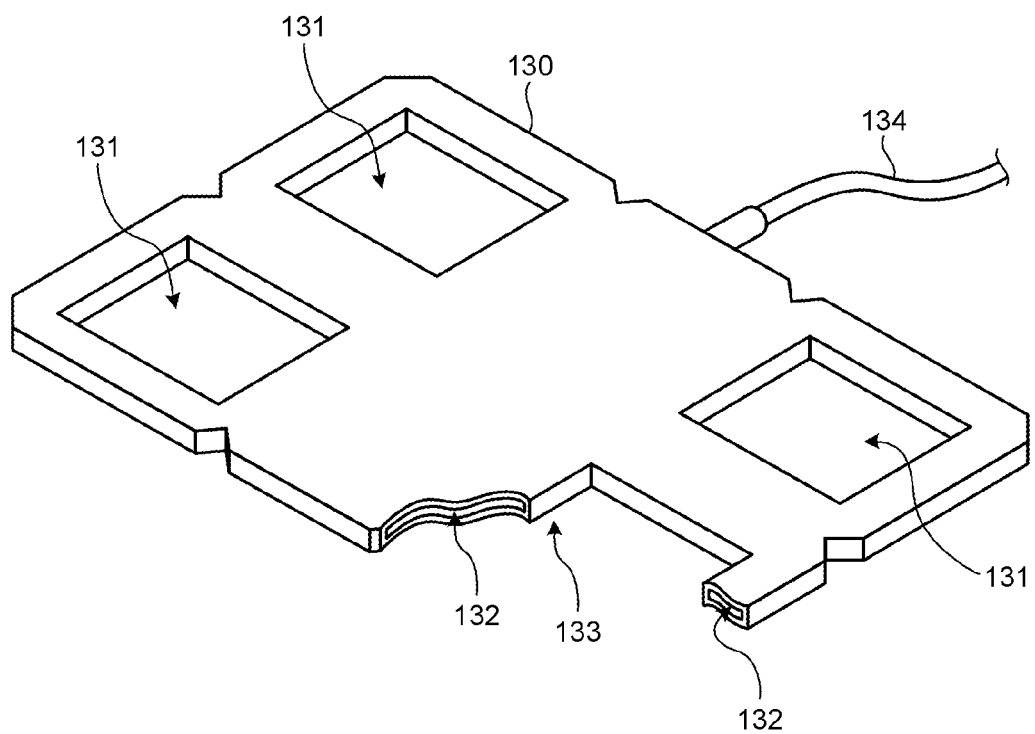
FIG. 4 is a view illustrating one example of the internal structure of the coil pad according to the first embodiment.

FIG. 4 is a view illustrating one example of an internal structure of the coil pad according to the first embodiment. For example, as illustrated in FIG. 4, the coil pad 130 according to the first embodiment has a hollow portion 132 inside. For example, as illustrated in FIG. 4, the hollow portion 132 is formed throughout the interior of a part of the coil pad 130 that does not correspond to the pad openings 131. A vibrating surface 133 is provided on one side (the reverse side of the coil pad 130 illustrated in FIG. 3) of the coil pad 130 that faces the subject S. The vibrating surface 133 vibrates when vibrating air is fed into the hollow portion 132. For example, air is fed into the hollow portion 132 from a vibration generating device (not illustrated) via an air supply pipe 134 attached to a long side section of the coil pad 130.

The position to which the air supply pipe 134 is attached is not necessarily limited to the long side section of the coil pad 130. For example, the air supply pipe 134 may be attached to a short side section of the coil pad 130, or be attached to a corner section thereof. The air supply pipe 134 may be attached to a surface of the coil pad 130 that faces the receiving coil 120 as long as the air supply pipe 134 does not overlap the receiving coil 120.

Figure 5:
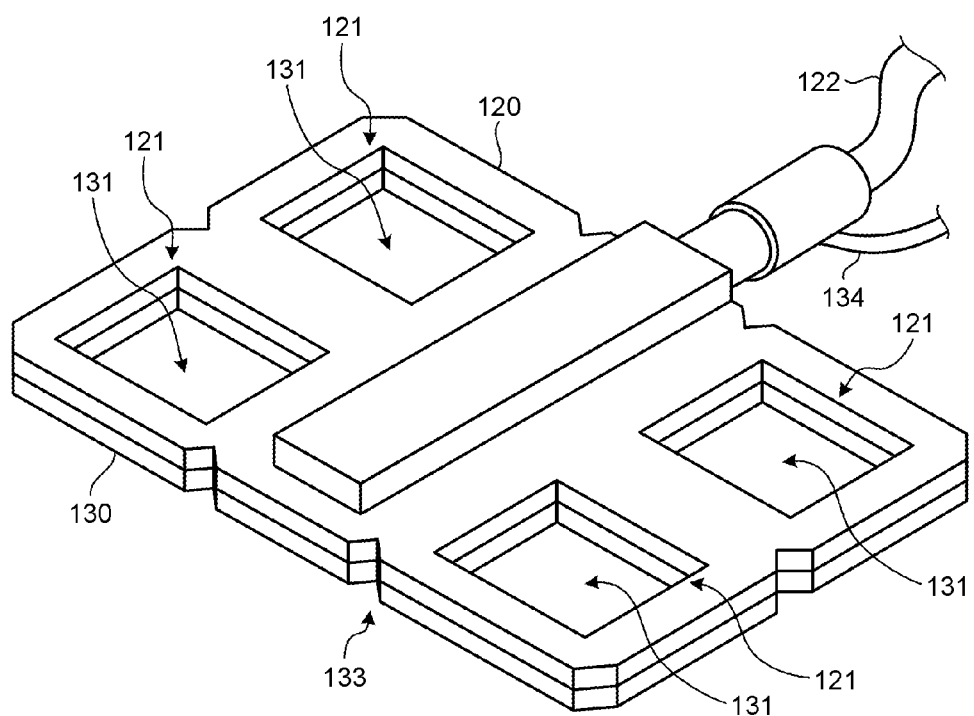
FIG. 5 is a view illustrating the coil pad according to the first embodiment with a receiving coil arranged thereon.

FIG. 5 is a view illustrating the coil pad according to the first embodiment with a receiving coil arranged thereon. As illustrated in FIG. 5, when the receiving coil 120 is placed on the coil pad 130, the pad openings 131 of the coil pad 130 are aligned with the coil openings 121 of the receiving coil 120, so that through-holes are formed between the coil openings 121 and the subject S. Subsequently, the receiving coil 120 and the coil pad 130 stacked on each other as illustrated in FIG. 5 are mounted on the subject S in such a manner that brings the vibrating surface 133 of the coil pad 130 into contact with the subject S.

In the first embodiment, the receiving coil 120 and the coil pad 130 stacked on each other are thus mounted in a manner that brings the vibrating surface 133 of the coil pad 130 into contact with the subject S. This makes it possible to use the coil pad 130 instead of a conventional vibrator in performing MR elastography.

Figure 6:
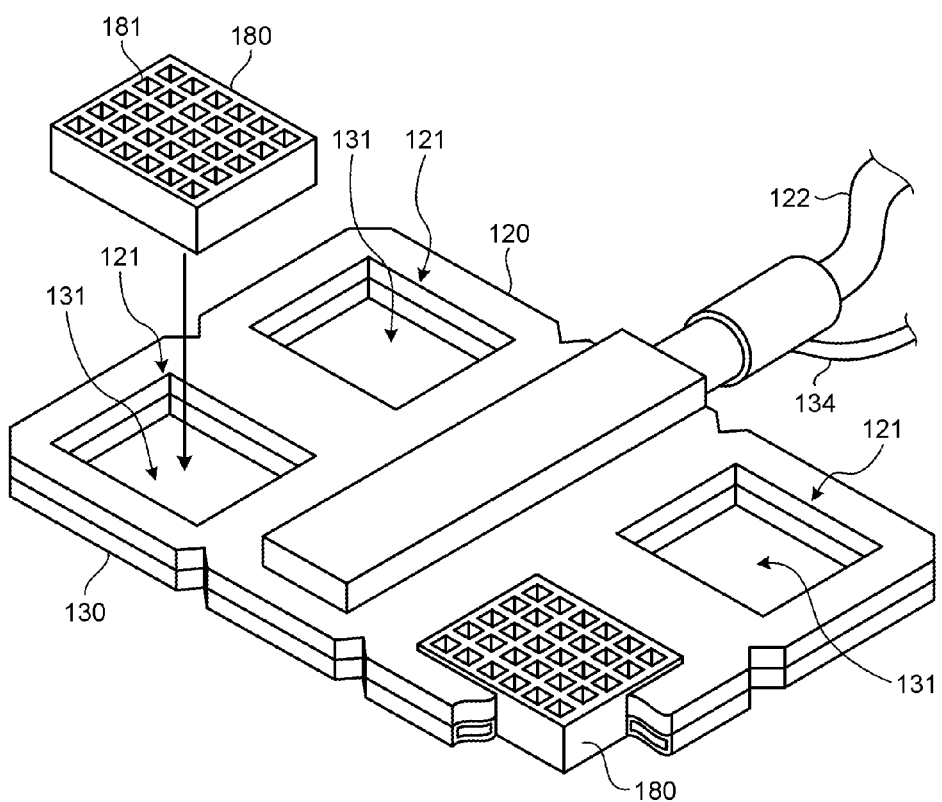
FIG. 6 is a view illustrating one example of a biopsy grid according to the first embodiment.

FIG. 6 is a view illustrating one example of a biopsy grid according to the first embodiment. For example, as illustrated in FIG. 6, a biopsy grid 180 according to the first embodiment is fitted in the receiving coil 120 and the coil pad 130 through the through-hole formed by the pad opening 131 between the coil opening 121 and the subject S. The biopsy grid 180 then serves as a guide when a biopsy puncture needle is inserted into the subject S. For example, as illustrated in FIG. 6, the biopsy grid 180 includes a plurality of adapter attaching portions 181 for fixing a puncture adapter attached to a puncture needle. In this example, for example, the respective adapter attaching portions 181 are holes each formed in a rectangular shape and are arranged into a plurality of rows and a plurality of columns.

In the first embodiment, the biopsy grid 180 is thus fitted in through the coil opening 121 of the receiving coil 120 and the pad opening 131 of the coil pad 130. This makes it possible to conduct a biopsy without having the receiving coil 120 and the coil pad 130 removed from the subject S after MR elastography is performed.

The first embodiment thus makes it possible to use the coil pad 130 in place of a vibrator when MR elastography is performed. The first embodiment further makes it possible to conduct a biopsy without having the coil pad 130 and the receiving coil 120 removed from the subject S after MR elastography is performed. For this reason, the first embodiment makes it possible to prevent displacement of a target position in a biopsy after elastography is performed.

The following describes other embodiments relating to a coil pad, a vibrator, and an MRI apparatus. The configurations of an MRI apparatus and a receiving coil according to each embodiment described below are basically the same as those in the first embodiment, with the only difference being that both or any one of the configurations of a coil pad and a vibrator is different. Accordingly, in each embodiment, descriptions of the configuration of an MRI apparatus and a receiving coil are omitted, and both or either of the configurations of a coil pad and a vibrator is described. In each embodiment described below, parts having the same functions as parts described in the first example are assigned the same reference numerals, and detailed descriptions thereof are omitted.

Second Embodiment

The first embodiment described above exemplifies a case where the hollow portion 132 is formed throughout the entire interior of the coil pad 130 other than portions corresponding to the pad openings 131. A second embodiment exemplifies another case where a plurality of hollow portions are formed inside a coil pad.

Figure 7:
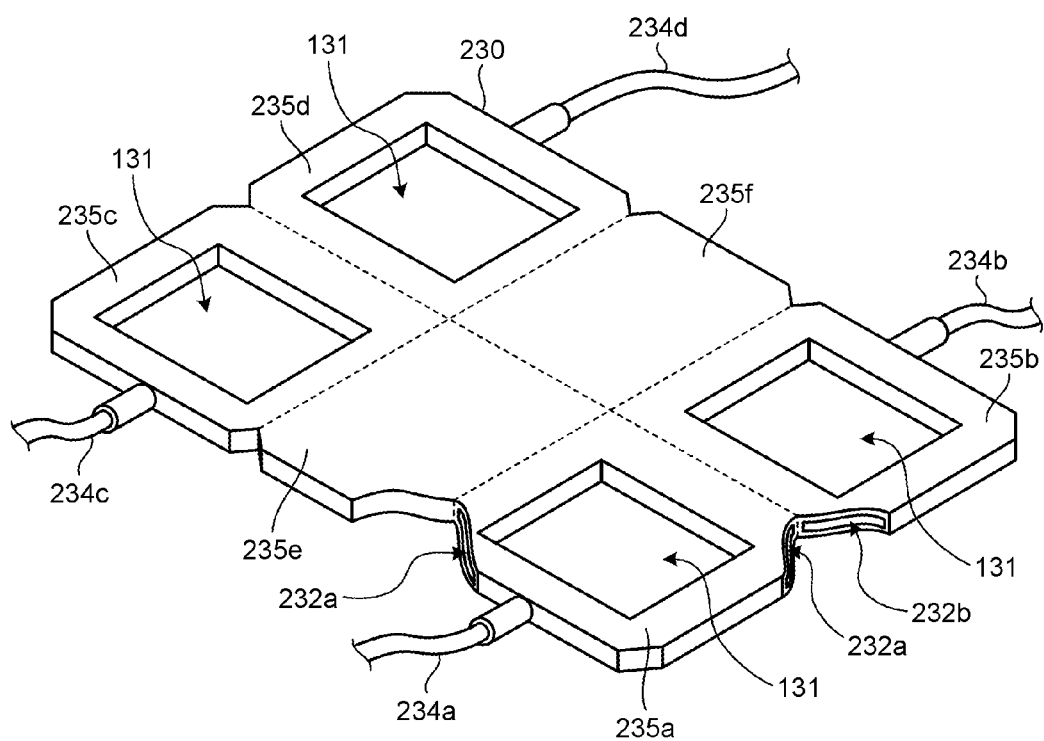
FIG. 7 is a view illustrating one example of a coil pad according to a second embodiment.

FIG. 7 is a view illustrating one example of a coil pad according to the second embodiment. For example, as illustrated in FIG. 7, the coil pad 230 according to the second embodiment includes six sections 235a to 235f, and a hollow portion is formed in the interior of each of the four sections 235a to 235d each including a pad opening 131. For example, as illustrated in FIG. 7, a hollow portion 232a is formed in the interior of the section 235a, and a hollow portion 232b is formed in the interior of the section 235b.

In this case, vibrating air is supplied into the respective hollow portions formed in the interior of the coil pad 230 via different air supply pipes. For example, air is supplied into the hollow portion 232a formed in the interior of the section 235a via an air supply pipe 234a, and air is supplied into the hollow portion 232b formed in the section 235b via an air supply pipe 234b. Air is supplied into the hollow portion (not illustrated) formed in the interior of the section 235c via an air supply pipe 234c, and air is supplied into the hollow portion (not illustrated) formed in the interior of the section 235d via an air supply pipe 234d.

Thus, in the second embodiment, the plurality of hollow portions are formed in the interior of the coil pad 230, and air is supplied into the respective hollow portions via the different air supply pipes. This makes it possible to locally vibrate the coil pad 130 when MR elastography is performed. Although FIG. 7 illustrates a case where air supply pipes are provided to all of the four sections 235a to 235d, an air supply pipe may be detachably provided. In such a case, an air supply pipe may be provided to any one or more of the four sections 235a to 235d that is desired to be vibrated. One or more hollow portions may be provided to a corresponding one or more of the four sections 235a to 235d.

Third Embodiment

The first and second embodiments exemplify cases where the biopsy grid 180 is fitted in through the through-hole formed by the pad opening 131 between the corresponding coil opening 121 and the subject S. A third embodiment exemplifies a case where a grid portion used in place of a biopsy grid is provided to a coil pad itself.

Figure 8:
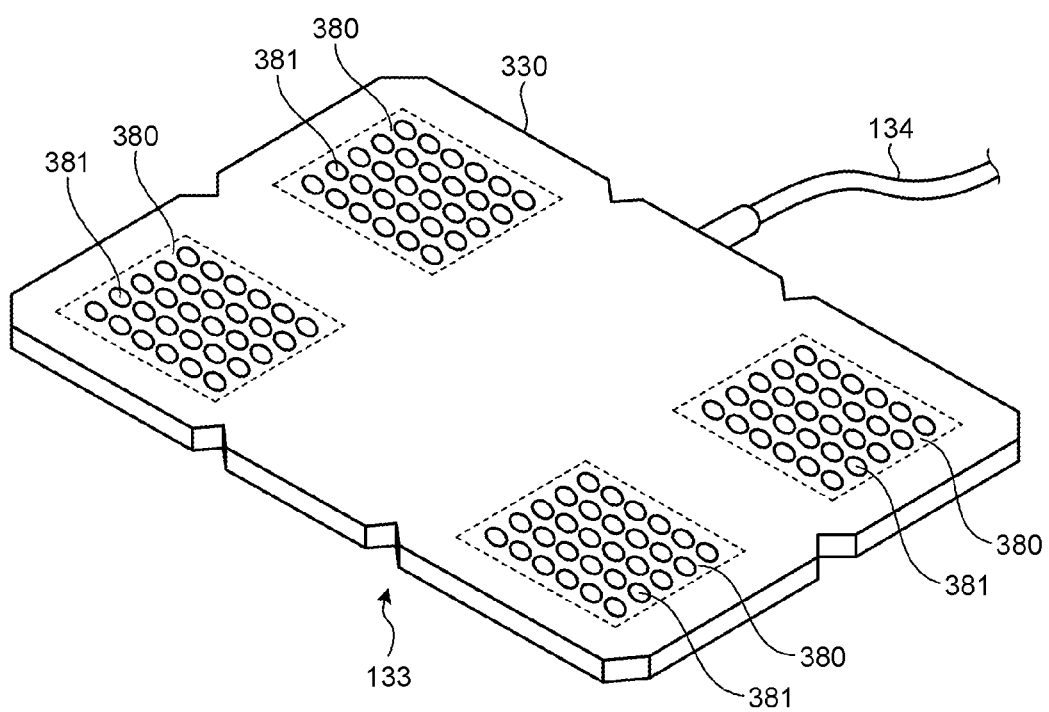
FIG. 8 is a view illustrating one example of a coil pad according to a third embodiment.

FIG. 8 is a view illustrating one example of a coil pad according to the third embodiment. For example, as illustrated in FIG. 8, a coil pad 330 according to the third embodiment has four grid portions 380 in positions corresponding to the four coil openings 121 of the receiving coil 120. Each of the grid portions 380 is aligned with the corresponding coil opening 121 of the receiving coil 120, and serves as a guide when a biopsy puncture needle is inserted into the subject S. For example, the grid portion 380 includes a plurality of puncture guiding holes 381 into which a puncture needle is inserted. For example, the puncture guiding holes 381 are holes each formed in a circular shape, and are arranged into a plurality of rows and a plurality of columns. It is desired that the peripheries of puncture guiding holes 381 be reinforced so as not to be damaged by a puncture needle.

Figure 9:
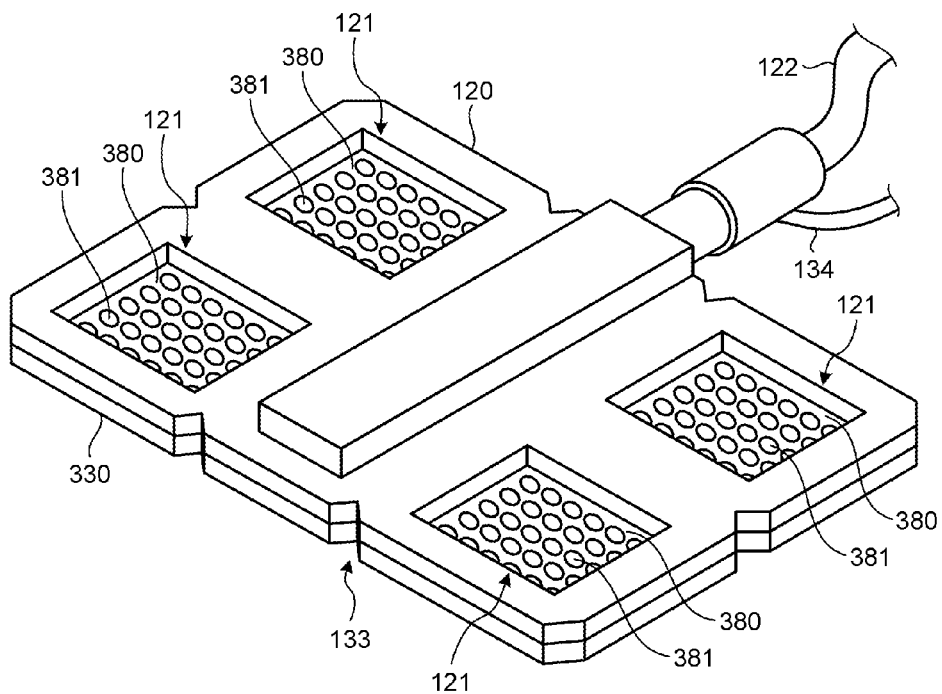
FIG. 9 is a view illustrating the coil pad according to the third embodiment with a receiving coil arranged thereon.

FIG. 9 is a view illustrating the coil pad according to the third embodiment with a receiving coil arranged thereon. As illustrated in FIG. 9, when the coil pad 330 has a receiving coil 120 arranged thereon, each of the grid portions 380 of the coil pad 330 is aligned with the corresponding coil opening 121 of the receiving coil 120. The receiving coil 120 and the coil pad 330, while being stacked on each other as illustrated in FIG. 9, is mounted on the subject S, in a manner that brings the vibrating surface 133 of the coil pad 330 into contact with the subject S In the third embodiment, the receiving coil 120 and the coil pad 130, while being stacked on each other, are thus mounted in a manner that brings the vibrating surface 133 of the coil pad 130 into contact with the subject S. This makes it possible to use the coil pad 130 in place of a conventional vibrator in performing MR elastography. In the third embodiment, a puncture can be performed through the coil opening 121 of the receiving coil 120 and the grid portion 380 of the coil pad 330. This makes it possible to conduct a biopsy without removing the receiving coil 120 and the coil pad 330 from the subject S after performing MR elastography. Thus, the third embodiment can prevent displacement of a biopsy target position after elastography.

Fourth Embodiment

The first to third embodiments exemplify cases where a coil pad is used in place of a vibrator since the coil pad vibrates when vibrating air is fed into a hollow portion formed in the interior of the coil pad. A fourth embodiment exemplifies a case where a vibrator is used.

Figure 10:
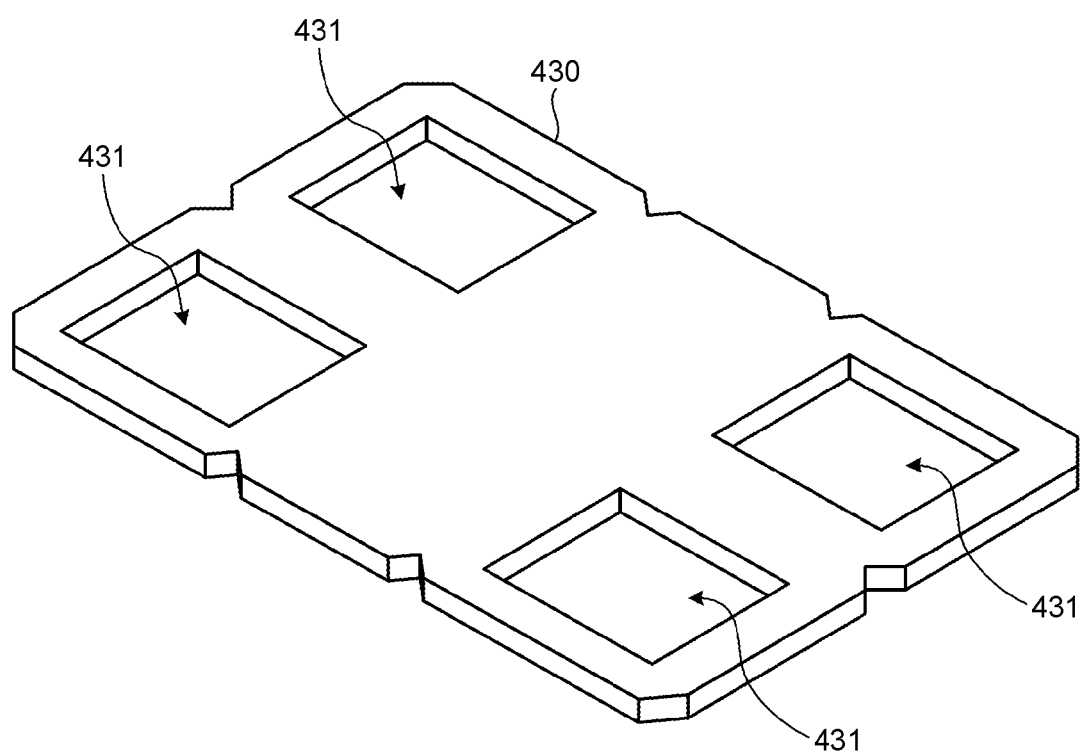
FIG. 10 is a view illustrating one example of a coil pad according to a fourth embodiment.

FIG. 10 is a view illustrating one example of a coil pad according to the fourth embodiment. For example, as illustrated in FIG. 10, a coil pad 430 according to the fourth embodiment is formed of a resin, such as vinyl chloride, and formed in substantially the same shape as that of the receiving coil 120. For example, when the receiving coil 120 illustrated in FIG. 2 is used, the coil pad 430 is formed in a rectangular shape as with the receiving coil 120. In the coil pad 430, four pad openings 431 are formed at positions corresponding to the positions of the coil openings 121 of the receiving coil 120. The four pad openings 431 have the same shapes as the respective coil openings 121. In this embodiment, the coil pad 430 according to the fourth embodiment includes no hollow portion in its interior.

The shape of the coil pad 430 need not necessarily be strictly the same as that of the receiving coil 120. Specifically, the coil pad 430 may be different in shape from the receiving coil 120 as long as at least one of the pad openings 431 is provided at a position that allows the pad opening 431 to be aligned with the corresponding coil openings 121 when the coil pad 430 is stacked on the receiving coil 120. The number of pad openings 431 of the coil pad 430 need not necessarily be strictly the same as the number of coil openings 121 of the receiving coil 120. Specifically, at least one of the pad openings 431 may be provided at a position that allows the pad opening 431 to be aligned with the corresponding coil opening 121 when the coil pad 430 is stacked on the receiving coil 120.

Figure 11:
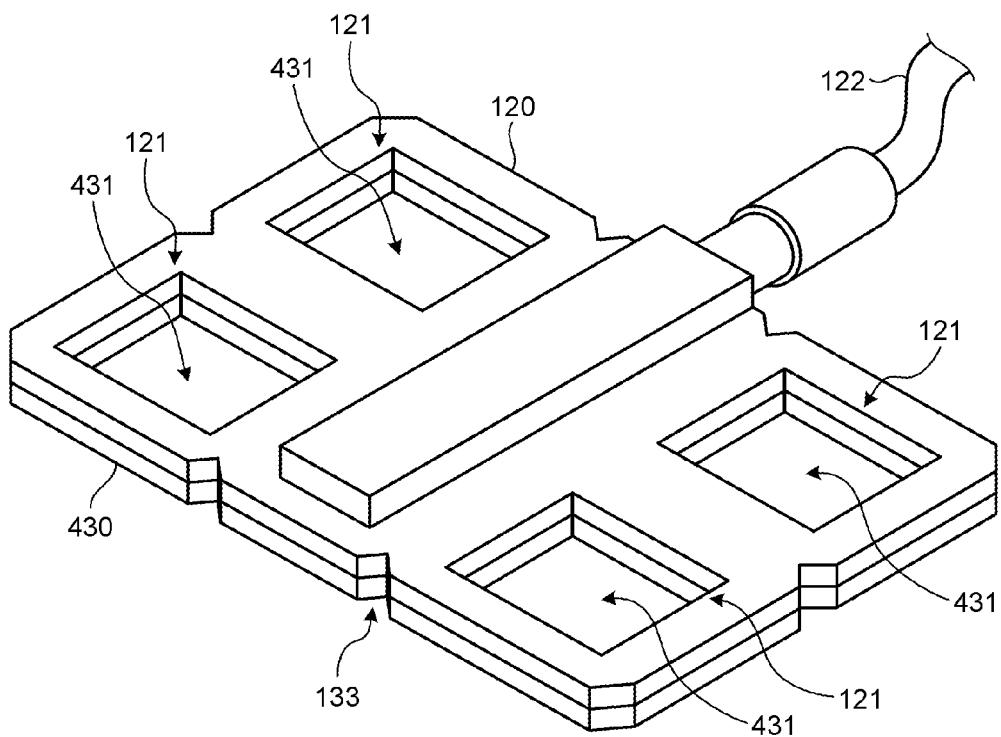
FIG. 11 is a view illustrating the coil pad according to the fourth embodiment with a receiving coil arranged thereon.

FIG. 11 is a view illustrating the coil pad according to the fourth embodiment with the receiving coil arranged thereon. As illustrated in FIG. 11, when the coil pad 430 has the receiving coil 120 arranged thereon, the pad openings 431 of the coil pad 430 are aligned with the coil openings 121 of the receiving coil 120, whereby a through-hole is formed between each of the coil openings 121 and the subject S. The receiving coil 120 and the coil pad 430, while being stacked on each other as illustrated in FIG. 11, are mounted on the subject S in a manner that brings the vibrating surface 133 of the coil pad 430 into contact with the subject S.

Figure 12:
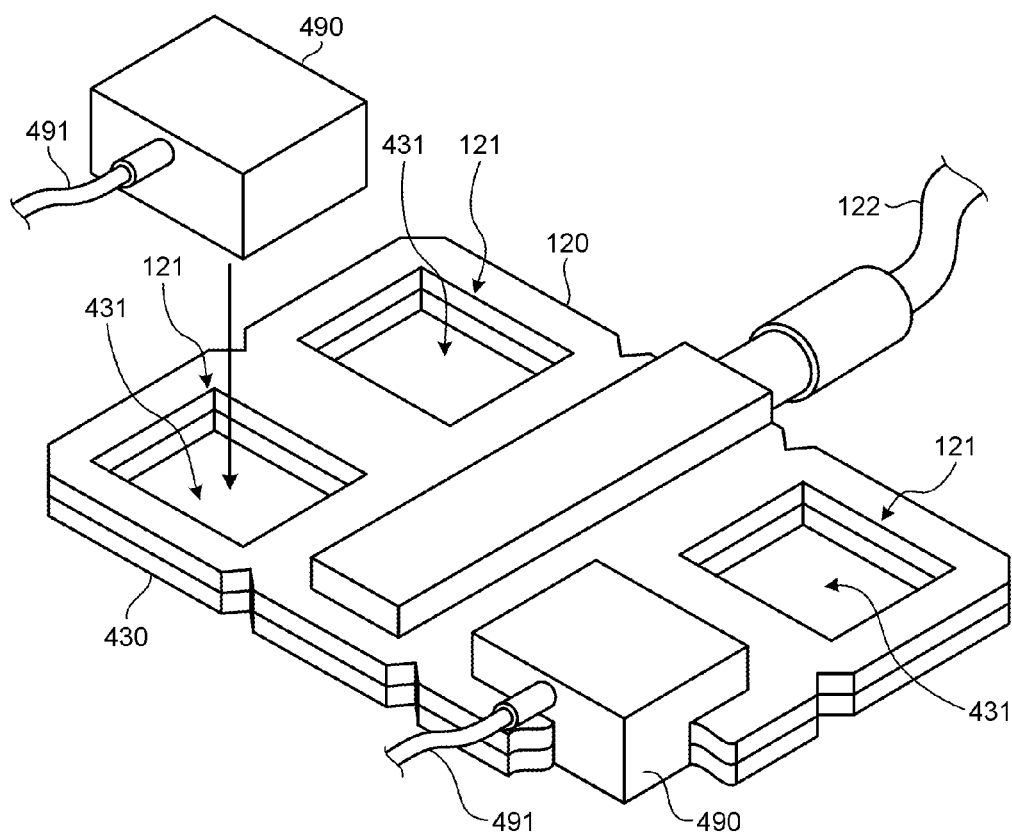
FIG. 12 is a view illustrating one example of a vibrator according to the fourth embodiment.

FIG. 12 is a view illustrating one example of a vibrator according to the fourth embodiment. For example, as illustrated in FIG. 12, a vibrator 490 according to the fourth embodiment is attached to the receiving coil 120 and the coil pad 430 through a through-hole formed by one of the pad openings 431 between the corresponding coil opening 121 and the subject S. When MR elastography is performed, the vibrator 490 vibrates the subject S by vibrating air fed into the interior thereof. For example, air is fed into the vibrator 490 from a vibration generating device (not illustrated) via an air supply pipe 491 attached to a side face section of the vibrator 490.

The position at which the air supply pipe 491 is attached is not necessarily limited to the side face section of the vibrator 490. For example, the air supply pipe 491 may be attached to the top face section of the vibrator 490, or may be attached to a corner section thereof. Specifically, for example, in the case of attaching the air supply pipe 491 to the side face section of the vibrator 490, the air supply pipe 491 is attached to a portion of the vibrator 490 that is exposed above the receiving coil 120 when the vibrator 490 is fitted in the receiving coil 120 and the coil pad 430.

Figure 13:
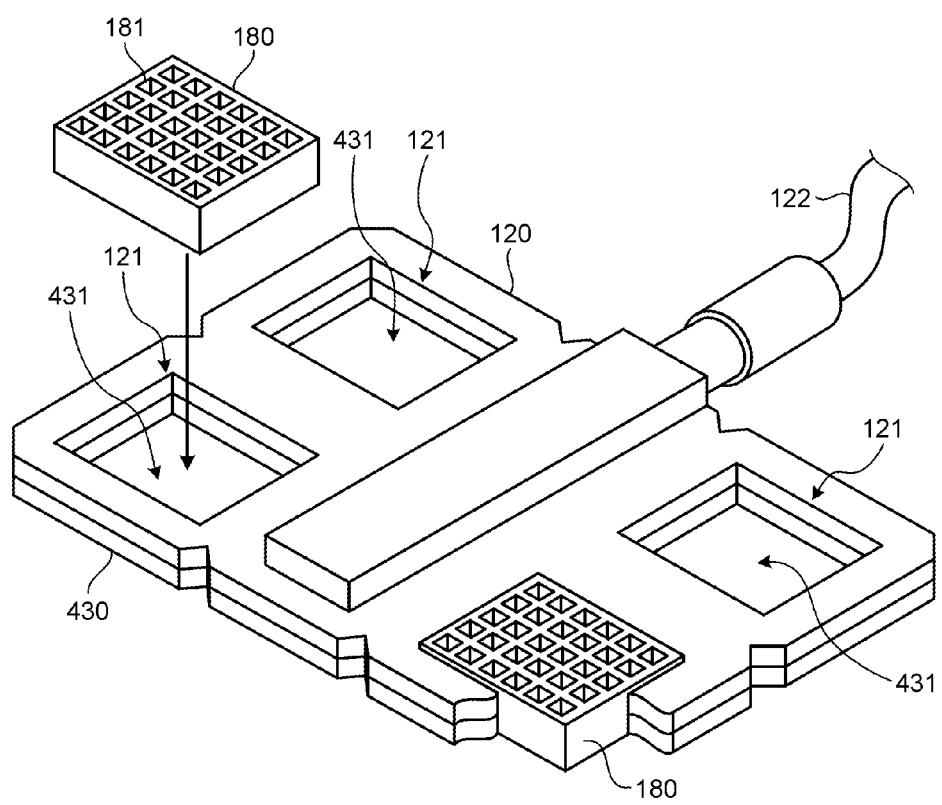
FIG. 13 is a view illustrating one example of a biopsy grid according to the fourth embodiment.

FIG. 13 is a view illustrating one example of a biopsy grid according to the fourth embodiment. For example, as illustrated in FIG. 13, a biopsy grid 180 according to the fourth embodiment is the same as the biopsy grid 180 described in the first embodiment. As illustrated in FIG. 13, when a biopsy is conducted on the subject, the biopsy grid 180 replaces the vibrator 490 to be fitted in the receiving coil 120 and the coil pad 430. Specifically, the biopsy grid 180 is fitted in the receiving coil 120 and the coil pad 430 through a through-hole formed by one of the pad openings 431 formed between the corresponding coil opening 121 and the subject S.

Thus, in the fourth embodiment, any one of the vibrator 490 and the biopsy grid 180 can be fitted in through the coil opening 121 of the receiving coil 120 and the pad opening 431 of the coil pad 430. This makes it possible to remove the vibrator 490 and fit the biopsy grid 180 in replacement thereof to conduct a biopsy without removing the receiving coil 120 and the coil pad 430 from the subject S, after performing MR elastography. Consequently, the fourth embodiment can prevent displacement of a biopsy target position after elastography.

In the fourth embodiment, the receiving coil 120 and the vibrator 490 may be secured to the subject S or the MRI apparatus 100 when elastography is performed. In such a case, for example, the vibrator 490 is secured to the subject S or the MRI apparatus 100 independently of the receiving coil 120 when it is fitted in through the coil opening 121 of the receiving coil 120 and the pad opening 431 of the coil pad 430.

Figure 14:
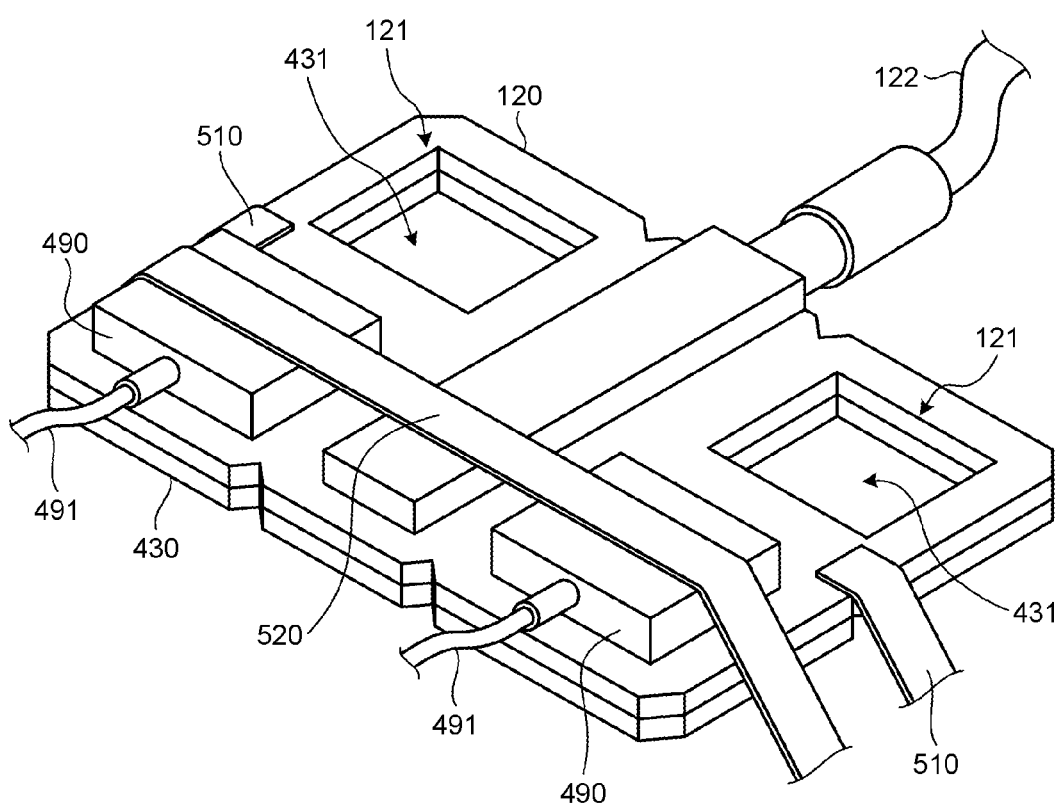
FIG. 14 is a view illustrating one example of a securing unit configured to secure a vibrator according to the fourth embodiment.

FIG. 14 is a view illustrating one example of a securing unit configured to secure a vibrator according to the fourth embodiment. For example, as illustrated in FIG. 14, a securing unit 510 secures the receiving coil 120 to a couchtop 161 or a couch apparatus 160, and a securing unit 520 secures the vibrators 490 to the couchtop 161 or the couch apparatus 160. In this case, for example, each of the securing units 510 and 520 is a foldable belt. In such a case, for example, the vibrators 490 are formed so as to be thicker than the receiving coil 120. This makes it possible to have only the vibrators 490 pressed and secured by the securing unit 510 when the securing unit 510 secures the vibrators 490 from above. The receiving coil 120 and the vibrator 490 may be secured to the subject S by the securing units 510 and 520, respectively.

The vibrator 490 is thus secured independently of the receiving coil 120. This makes it possible to suppress vibration to be transmitted to the receiving coil 120 so that only the vibration from the subject S may be transmitted thereto. Although this embodiment exemplifies a case where a foldable belt or the like is used as each of the securing units, a support having stiffness may be used. In such a case, the securing units hold the receiving coil 120 and the vibrator 490 to securing positions independently of each other. This makes it possible to further suppress vibration that is transmitted to the receiving coil 120.

Furthermore, when the vibrators 490 are fitted in through the coil openings 121 of the receiving coil 120 and the pad openings 431 of coil pad 430, the vibrators 490 may be positioned in a predetermined state.

For example, each of the vibrators 490 has a vibrating surface that is vibrated by air fed thereto. In such a case, for example, the vibrator 490 has a positioning portion configured to position the vibrator 490 in a manner that the vibrating surface is arranged so as to face the subject S when the vibrator 490 is fitted in through the coil opening 121 and the pad opening 431.

Figure 15:
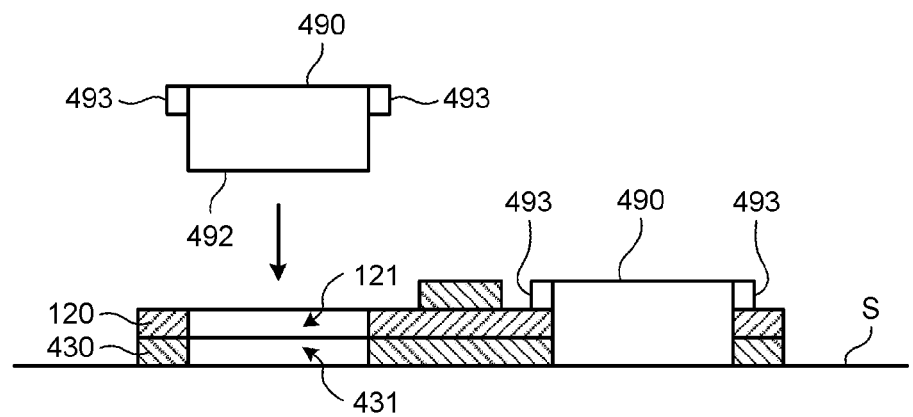
FIG. 15 is a view illustrating one example of a vibrator according to a modification of the fourth embodiment.

FIG. 15 is a view illustrating one example of a vibrator 490 according to a modification of the fourth embodiment. FIG. 15 illustrates a cross section taken along a line passing through the two coil openings 121 of the receiving coil 120, a cross section taken along a line passing through the two pad openings 431 of the coil pad 430, and the vibrators 490.

For example, as illustrated in the left side of FIG. 15, each of the vibrators 490 has a vibrating surface 492 that is arranged so as to face the subject S. For example, the vibrator 490 further has a positioning portion 493 that is provided so as to project from a side face section of the vibrator 490. The positioning portion 493 is provided on the side face section of the vibrator 490 and far from the vibrating surface 492. Specifically, the positioning portion 493 is provided on the side face section of the vibrator 490 and near the opposite surface of the vibrating surface.

Thus, as illustrated in the right side of FIG. 15, when the vibrator 490 is fitted in through the coil opening 121 and the corresponding pad opening 431 from above the receiving coil 120, the positioning portion 493 abuts the upper surface of the receiving coil 120, whereby the vibrator 490 is positioned. Since the positioning portion 493 is provided at a position far from the vibrating surface 492 on the side face section of the vibrator 490, the vibrator 490 is consequently positioned in a manner that the vibrating surface 492 is placed facing downward, that is, facing the subject S.

The shape of the positioning portion 493 of the vibrator 490 is not limited to the illustrated one, and the positioning portion 493 may have any different shape that allows the vibrating surface 492 to be placed facing the subject S when the vibrator 490 is fitted in. The positioning portion 493 may be provided to all of the side surfaces of the vibrator 490 or provided to one or some of the sides thereof.

In another example, the vibrator 490 includes a positioning portion configured to position the vibrator 490 when the vibrator 490 is fitted in through the coil opening 121 and the pad opening 431 so that the air supply pipe 491 may be placed along a moving direction of the couchtop 161 on which the subject S is to be laid.

Figure 16:
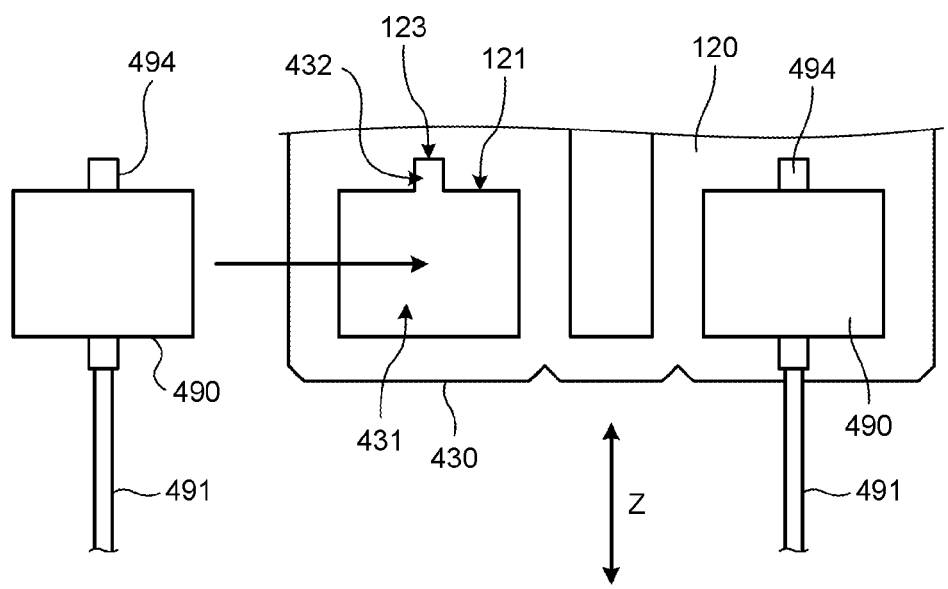
FIG. 16 is a view illustrating one example of a vibrator according to another modification of the fourth embodiment

FIG. 16 is a view illustrating one example of a vibrator according to another modification of the fourth embodiment. FIG. 16 illustrates two coil openings 121 of the receiving coil 120 when they are viewed from above, and two vibrators 490. The two coil openings 121 illustrated in FIG. 16 are assumed to be arranged in a row along a direction substantially orthogonal to the moving direction z of the couchtop 161.

For example, as illustrated in the left side of FIG. 16, each of the vibrators 490 includes, as a positioning portion, a positioning projection 494 provided on the opposite side of a side to which the air supply pipe 491 is attached. In contrast, a positioning recess 123 is formed on each of the coil openings 121 of the receiving coil 120. The shape of the positioning recess 123 fits to the positioning projection 494. A positioning recess 432 is further formed on each of the pad openings 431 of the coil pad 430 and at a position that would correspond to the positioning recess 123 when the coil pad 430 and the receiving coil 120 are aligned with each other. The shape of the positioning recess 432 fits to the positioning projection 494.

In this case, when the vibrator 490 is fitted in through the coil opening 121 and the pad opening 431, the positioning recesses 123 and 432 are provided at positions that allow them to fit to the positioning projection 494 of the vibrator 490 with the air supply pipe 491 of the vibrator 490 placed along the moving direction of the couchtop 161, for example, as illustrated in the right side of FIG. 16. The vibrator 490 is consequently positioned in a manner that the air supply pipe 491 is placed extending in the moving direction of the couchtop 161.

Here, the positions at which the positioning projection 494 of the vibrator 490, the positioning recess 123 of the receiving coil 120, and the positioning recess 432 of the coil pad 430 are formed are not necessarily limited to the illustrated positions. The positioning projection 494, the positioning recess 123, and the positioning recess 432 of the coil pad 430 may be formed at any positions that allow them to fit to one another with the supply pipe 491 of the vibrator 490 placed along the moving direction of the couchtop 161. The shapes of the positioning projection 494 of the vibrator 490, the positioning recess 123 of the receiving coil 120, and the positioning recess 432 of the coil pad 430 are not necessarily limited to the illustrated ones, and may be any other shapes that allow them to fit to one another.

Both the positioning portion 493 and the positioning projection 494 may be provided to the vibrator 490.

Although each of the above-described embodiments exemplifies a case where the medium that transmits vibration is air, embodiments are not limited to such a case. For example, the medium may be a gas other than air or be liquid. The medium used here is desirably the one that does not emit magnetic resonance signals, and, for example, heavy water is used.

Although each of the first to third embodiments described above exemplifies a case where a coil pad is provided, as a vibrating portion, facing the subject S and has a vibrating surface that is vibrated by the medium, embodiments are not limited to such a case. That is, a portion other than the vibrating surface may vibrate in the coil pad. For example, the entirety of the coil pad may function as a vibrating portion. However, when the receiving coil 120 vibrates, it may possibly affect magnetic resonance signals to be received by the receiving coil 120. For this reason, the vibrating portion desirably has a structure that can minimize transmission of vibration of the coil pad to the receiving coil 120. For example, the coil pad may have a structure that vibrates only the vibrating surface placed facing the subject S or that vibrates only a portion thereof located near the vibrating surface. By this structure, vibration to be transmitted to the receiving coil 120 can be suppressed.

According to at least one of the above-described embodiments, displacement of a biopsy target position after elastography can be prevented.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An magnetic resonance imaging (MRI) radio frequency (RF) coil pad configured to fit between (a) an MRI RF receiving coil and (b) a subject while the subject is being imaged when the RF receiving coil is mounted on the subject and receiving magnetic resonance signals emitted from the subject during MRI, the coil pad comprising:
   a pad opening configured to align with an RF coil opening included in the RE receiving coil thereby forming a through-hole between the RF coil opening and the pad opening to the subject; and
   a fluid conduit connected to pass a supply of vibrating fluid to a pad hollow portion filled with a fluid medium that transmits vibration in the medium to the subject through a wall of the hollow portion.

2. The coil pad according to claim 1, wherein said coil pad is configured to accept a biopsy grid fitted into the coil pad through the through hole and used as a guide when a biopsy puncture needle is inserted into the subject.

3. The coil pad according to claim 1, wherein the pad opening includes a grid portion that provides a guide when a biopsy puncture needle is inserted into the subject.

4. The coil pad according to claim 1, wherein the fluid medium is air.

5. The coil pad according to claim 1, wherein said wall of the hollow portion provides a vibrating surface on one side of the pad facing the subject.

6. A magnetic resonance imaging (MRI) apparatus comprising:
   an MRI radio frequency (RF) receiving coil configured to be mounted on a subject and to receive magnetic resonance signals emitted from the subject; and
   a coil pad configured to fit between the RF receiving coil and the subject, wherein the coil pad includes:
      a pad opening configured to align with an RF coil opening included in the RF receiving coil thereby forming a through-hole between the RF coil opening and the pad opening to the subject, and
      a fluid conduit connected to pass a supply of vibrating fluid to a pad hollow portion filled with a fluid medium that transmits vibrations in the medium to the subject through a wall of the hollow portion.

* * * * *